United States Patent
Kobashigawa et al.

(10) Patent No.: US 6,232,367 B1
(45) Date of Patent: *May 15, 2001

(54) OPALESCENT FILLERS FOR DENTAL RESTORATIVE COMPOSITES

(75) Inventors: Alvin I. Kobashigawa, Laguna Beach; Christos Angeletakis, Orange, both of CA (US)

(73) Assignee: Kerr Corporation, Orange, CA (US)

(*) Notice: Subject to any disclaimer, the term of this patent is extended or adjusted under 35 U.S.C. 154(b) by 0 days.

This patent is subject to a terminal disclaimer.

(21) Appl. No.: 09/413,762

(22) Filed: Oct. 7, 1999

(51) Int. Cl.$^7$ .............................. A61K 6/083; C08K 3/36
(52) U.S. Cl. ...................... 523/116; 523/115; 523/220; 524/413; 524/558; 526/301; 260/998.11; 260/998.17
(58) Field of Search ................ 523/116; 524/431, 524/493, 494, 558; 526/301; 260/998.11, 998.17

(56) References Cited

U.S. PATENT DOCUMENTS

| | | |
|---|---|---|
| Re. 32,073 | 1/1986 | Randklev . |
| Re. 32,299 | 12/1986 | Randklev . |
| 4,215,033 | 7/1980 | Bowen . |
| 4,217,264 | 8/1980 | Mabie et al. . |
| 4,267,097 | 5/1981 | Michl et al. . |
| 4,281,991 | 8/1981 | Michl et al. . |
| 4,306,913 | 12/1981 | Mabie et al. . |
| 4,350,532 | 9/1982 | Randklev . |
| 4,358,549 | 11/1982 | Randklev . |
| 4,374,937 | 2/1983 | Nemcek et al. . |
| 4,386,912 * | 6/1983 | Nagase et al. . |
| 4,396,377 | 8/1983 | Roemer et al. . |
| 4,396,476 | 8/1983 | Roemer et al. . |
| 4,407,984 | 10/1983 | Ratcliffe et al. . |
| 4,427,823 | 1/1984 | Inagaki et al. . |
| 4,433,959 | 2/1984 | Faunce . |
| 4,459,193 | 7/1984 | Ratcliffe et al. . |
| 4,500,657 * | 2/1985 | Kumar . |
| 4,602,076 | 7/1986 | Ratcliffe et al. . |
| 4,698,373 | 10/1987 | Tateosian et al. . |
| 4,744,759 | 5/1988 | Bowen . |
| 4,778,834 | 10/1988 | Murray . |
| 4,920,082 | 4/1990 | Danielson . |
| 5,304,586 | 4/1994 | Hammesfahr et al. . |
| 5,308,243 | 5/1994 | Emmons . |
| 5,308,886 | 5/1994 | Masuhara et al. . |
| 5,312,484 | 5/1994 | Kaliski . |
| 5,360,770 | 11/1994 | Chadwick . |
| 5,432,130 | 7/1995 | Rheinberger et al. . |
| 5,470,231 | 11/1995 | Stern . |
| 5,502,087 | 3/1996 | Tateosian et al. . |
| 5,584,886 * | 12/1996 | Lai . |
| 5,618,763 | 4/1997 | Frank et al. . |
| 5,622,551 | 4/1997 | Erbe et al. . |
| 5,708,051 * | 1/1998 | Erdrich et al. . |
| 5,747,050 | 5/1998 | Tolpa et al. . |
| 5,773,489 | 6/1998 | Sato . |
| 6,121,344 * | 9/2000 | Angeletakis et al. ............... 523/116 |

FOREIGN PATENT DOCUMENTS

| | | |
|---|---|---|
| 0 533 434 | 3/1993 | (EP) . |
| WO 90/08799 | 8/1990 | (WO) . |

* cited by examiner

Primary Examiner—Peter Szekely
(74) Attorney, Agent, or Firm—Wood, Herron & Evans, LLP

(57) ABSTRACT

There is provided a resin-containing dental composite including a dispersed phase, reinforcing, translucent filler having about 25–80% by volume of the filler particles in the particle size range from about 0.2 μm to about 0.6 μm whereby the composite has a self-opalescing quality. Without the addition of opalescence-imparting pigments, a dental restorative composite is provided that displays opalescence to the visible eye, which gives the restoration the appearance of a vital, natural tooth. Preferably, the refractive indices of the resin and the translucent filler are the same or substantially similar, both advantageously being within the range of 1.45–1.60. Further, to prevent the opal effect from being masked, the dental restorative composite advantageously comprises less than 0.0021% by weight yellow hue pigments such that the composite formulation is relatively colorless.

28 Claims, No Drawings

OPALESCENT FILLERS FOR DENTAL RESTORATIVE COMPOSITES

FIELD OF THE INVENTION

The present invention is generally related to a composite resin material used for dental restoration, and more particularly to a universal composite resin material suitable for all dental restorations incorporating a self-opalescing translucent filler.

BACKGROUND OF THE INVENTION

In dentistry, practitioners use a variety of restorative materials to create crowns, veneers, direct fillings, inlays, onlays and splints. One of the major goals in restorative dentistry is to produce restorations that match the esthetics of the natural tooth. Highly esthetic tooth colored restorations were first introduced to dentistry in the 1940's with acrylic resins and silicate cements. These were direct filling restorations that were tooth colored and translucent in visible light like natural teeth. When placed in the mouth, the fillings were not easily discernible from the tooth itself. In the 1950's, dental porcelains were introduced, which provided a variety of shades and translucencies to further improve the esthetics of the restorations. These were used in restorations, such as porcelain fused to metal crowns and bridges, or in inlays, onlays and veneers. Tooth shading with porcelain restorations has been highly successful and has become state-of-art in the industry today. In the 1970's, fluorescence was incorporated into dental porcelains, which further improved the esthetics of dental restorations and made them more natural appearing, especially under fluorescent lighting conditions. More recently, in the 1990's, opalescence has been incorporated into dental porcelains to produce the natural "opal effect" present in natural teeth.

Translucency, shading, fluorescence and opalescence are optical properties that give the natural tooth its vital-looking appearance. Translucency and shading have the greatest impact on the total vitality of the tooth because they are the most readily observed. Dentin and enamel are both translucent, but enamel is more translucent, almost transparent and colorless. The color or shade of the tooth mostly comes from dentin and is transmitted through the enamel layer to the surface of the tooth. Enamel is a highly mineralized crystalline structure composed of millions of enamel rods or prisms. As light travels through the enamel, the rods scatter and transmit the rays to the tooth surface much like a fiber optic system. Enamel, though highly transparent, does not transmit light like a clear window glass. Instead, the enamel diffuses the light, rendering the enamel opalescent.

Fluorescence and opalescence are more subtle optical properties that further enhance the natural-looking, life-like appearance or "vitality" of the tooth. Fluorescence is defined as the emission of electromagnetic radiation that is caused by the flow of some form of energy into the emitting body, which ceases abruptly when the excitation ceases. In natural teeth, components of the enamel, including hydroxyapatite, fluoresce under long wavelength ultraviolet light, emitting a white visible light. This phenomenon is subtle in natural daylight but still adds further to the vitality of the tooth. In contrast, under certain lighting conditions, the lack of fluorescence in a restorative material may become alarming. Under "black light" conditions, such as that often used in discotheque-type night clubs, if a restoration does not fluoresce, the contrast between the tooth and restoration may be so great that the tooth may actually appear to be missing.

Opalescence is defined as the milky, iridescent appearance of a dense, transparent medium or colloidal system when illuminated by visible light. It is best illustrated by the mineral opal, which is a natural hydrated form of silica. The "opal effect" is a light scattering phenomenon in translucent materials that produces a blue effect in reflected light due to the scattering of short wavelength light and an orange effect in transmitted light. This effect is different from simple reflected light in translucent materials and produces the milky iridescent effect present in the natural tooth. Restorations that are not opalescent do not have the vital looking appearance of a natural tooth itself.

Without being bound by theory, the chemistry and structure of enamel may be responsible for the "opal effect." Chemically, tooth enamel is a highly mineralized crystalline structure containing from 90% to 92% hydroxy apatite by volume. Structurally, it is composed of millions of enamel rods or prisms aligned perpendicular to the dentinoenamel junction and extending to the tooth surface. The enamel rods measure about 4–8 $\mu$m in diameter and the head or body section at the surface of the rods is about 5 $\mu$m wide. The crystallites are tightly packed in a distinct pattern or orientation that gives strength, hardness and structural identity to the enamel prisms. The particle size and crystalline orientation of the enamel prisms likely are responsible for producing the light scattering "opal effect."

Although opalescence has been incorporated into dental porcelains, the current trend in dental restorative technology is to use composite resins for restoration, rather than the porcelains. Composite resins are a type of restorative material which are suspensions of strengthening agents, such as mineral filler particles, in a resin matrix. These materials may be dispersion-reinforced, particulate-reinforced, or hybrid composites.

Dispersion-reinforced composites include a reinforcing filler of, for example, fumed silica having a mean particle size of about 0.05 $\mu$m or less, with a filler loading of about 30%–45% by volume. Because of the small particle size and high surface area of the filler, the filler loading into the resin is limited by the ability of the resin to wet the filler. Consequently, the filler loading is limited to about 45% by volume. Due to the low loading, the filler particles are not substantially in contact with one another. Thus, the primary reinforcing mechanism of such dispersion-reinforced composites is by dislocation of flaws in the matrix around the filler. In dispersion-reinforced materials, the strength of the resin matrix contributes significantly to the total strength of the composite. In dentistry, dispersion-reinforced composite resins or microfills are typically used for cosmetic restorations due to their ability to retain surface luster. Typically, these microfill resins use free radical-polymerizable resins such as methacrylate monomers, which, after polymerization, are much weaker than the dispersed filler. Despite the dispersion reinforcement, microfill resins are structurally weak, limiting their use to low stress restorations.

One example of a dispersion-reinforced composite is HELIOMOLAR®, which is a dental composite including fumed silica particles on the order of 0.05 $\mu$m mean particle size and rare earth fluoride particle on the order of less than 0.2 $\mu$m mean particle size. HELIOMOLAR® is a radiopaque microfill-type composite available from Vivadent. The rare earth fluoride particles contribute to both flexural strength and radiopacity.

Particulate-reinforced composites typically include a reinforcing filler having an average particle size greater than about 0.6 $\mu$m and a filler loading of about 60% by volume. At these high filler loadings, the filler particles begin to contact one another and contribute substantially to the reinforcing mechanism due to the interaction of the particles with one another and to interruption of flaws by the particles themselves. These particulate-reinforced composite resins are stronger than microfill resins. As with the dispersion-reinforced composites, the resin matrix typically includes methacrylate monomers. However, the filler in particulate-reinforced composites has a greater impact on the total strength of the composite. Therefore, particulate-reinforced composites are typically used for stress bearing restorations.

Another class of dental composites, known as hybrid composites, include the features and advantages of dispersion reinforcement and those of particulate reinforcement. Hybrid composite resins contain fillers having an average particle size of 0.6 μm or greater with a microfiller having an average particle size of about 0.05 μm or less. HERCULITE® XRV (Kerr Corp.) is one such example. HERCULITE® is considered by many as an industry standard for hybrid composites. It has an average particle size of 0.84 μm and a filler loading of 57.5% by volume. The filler is produced by a wet milling process that produces fine particles that are substantially contaminant free. About 10% by volume of this filler exceeds 1.50 μm in average particle size. In clinical use, the surface of HERCULITE® turns to a semi-glossy matte finish over time. Because of this, the restoration may become distinguishable from normal tooth structure when dry, which is not desirable for a cosmetic restoration.

Another class of composites, flowable composites, have a volume fraction of structural filler of about 10% to about 30% by volume. These flowable composites are mainly used in low viscosity applications to obtain good adaptation and to prevent the formation of gaps during the filling of a cavity.

Various methods of forming submicron particles, such as precipitation or sol gel methods, are available to produce particulate reinforcing fillers for hybrid composites. Comminution by a milling method may also be used for forming the submicron particles. The predominant types of milling methods are dry milling and wet milling. In dry milling, air or an inert gas is used to keep particles in suspension. However, fine particles tend to agglomerate in response to van der Waals forces, which limits the capabilities of dry milling. Wet milling uses a liquid such as water or alcohol to control agglomeration of fine particles. Therefore, wet milling is typically used for comminution of submicron-sized particles. As opposed to the spherically-shaped particles typically produced by sol gel methods, the ground particles are nonspherical, providing increased adhesion of the resin to the structural filler, thereby further enhancing the overall strength of the composite.

In co-pending U.S. patent application Ser. No. 09/270,999 now U.S. Pat. No. 6,121,344, entitled "Optimum Particle Sized Hybrid Composite," C. Angeletakis et al., filed on Mar. 17, 1999 and incorporated herein by reference in its entirety, there is disclosed a resin-containing dental composite including a translucent structural filler of ground particles having an average particle size of between about 0.05 μm and about 0.5 μm that has the high strength required for load bearing restorations, yet maintains a glossy appearance in clinical use required for cosmetic restorations. Specifically, since the structural filler size is less than the wavelength of visible light, the surface of a dental restoration will reflect more light in some directions than in others even after wear of the composite by brushing. The visible light waves do not substantially interact with the structural filler particles protruding out of the surface of the composite, and therefore, haze is reduced and the luster of the surface is maintained even after substantial brushing. This application represents a significant advancement in hybrid composite technology, but some of the composites produced according to the teachings of this pending application lack the vital looking appearance of a natural tooth.

As can be discerned from the multitude of patents in the area of dental restorative materials, the development of composite resins for dental restorations has been extremely difficult, attempting to balance physical properties with optical properties to produce an overall superior product. Pursuit of the "opal effect" in composite resins has mainly focused on small additions of "opal agents" or pigments, such as microfine titania, alumina or zirconia to achieve opalescence. For example, European Publication No. 533, 434 describes the addition of microfine titania (<0.2μm) in an amount less than 2 wt. % to hybrid or microfill cold-polymerizable dental composite formulations to achieve opalescence.

It is desirable to achieve opalescence in both hot- and cold-polymerizable dental composite resins, particularly the composite described in the copending application Ser. No. 09/270,999. While opalescence may be achieved by modifying the composite formulations with small amounts of opal agents or pigments, the present invention focuses on the development of a self-opalescing composite resin.

SUMMARY OF THE INVENTION

The present invention provides a resin-containing dental composite including a dispersed phase, reinforcing, translucent filler having about 15–80% by volume of these filler particles in the particle size range between about 0.2 μm and about 0.6 μm whereby the composite has a self-opalescing quality. Without the addition of opalescence-imparting pigments, the dental restorative composite of the present invention displays opalescence to the visible eye, which gives the restoration the appearance of a vital, natural tooth. To this end, and in accordance with the principles of the present invention, opalescence as defined herein by an average $\Delta C^*_{T-R}$ coordinate of at least about 9 is achieved by incorporating into a resin matrix a translucent filler, preferably at a loading between about 20–86% by weight of the composite, in which about 15–80% by volume, and preferably 25–80% by volume, of this filler component has particles in the size range of about 0.2–0.6 μm.

In a further feature of the present invention, the refractive indices of the resin and the translucent filler are the same or substantially similar, both being within the range of 1.45–1.60. More particularly, it is preferred that the refractive index of the filler be within +/−0.04 of the refractive index of the resin. In yet a further feature of the present invention, to prevent the opal effect achieved by the present invention from being masked, the dental restorative composite comprises less than 0.0021% by weight yellow hue pigments such that the composite formulation is relatively colorless, much like human enamel.

In a preferred embodiment of the present invention, the filler is ground, typically by agitator or vibratory milling, to the preferred particle size range. As opposed to the particles formed by the known sol-gel process, the grinding of the filler results in nonspherical particles which due to their irregular shape interact with the polymerized resin to a much greater extent to increase adhesion of the resin to the filler and thereby increase the overall strength of the composite.

In accordance with a further aspect of the invention, microfill particles having a mean particle size less than about 0.05 μm may be added, preferably between about 1% by weight and about 15% by weight of the composite to form a hybrid composite. The microfill particles contribute to dispersion reinforcement, fill the interstices between the larger structural filler particles reducing occluded volume, and provide a large surface area to be wetted by the resin to increase strength. The microfill particles also contribute to the flow properties of the uncured resin.

DETAILED DESCRIPTION OF THE INVENTION

The present invention, in a preferred form, is a dental restorative composite that includes a translucent filler having sufficient particles in the particle size range between about 0.2 μm and about 0.60 μm whereby the composite is self-opalescing. The opalescence produced by the translucent, reinforcing fillers is less pronounced than that achieved by the addition of opalescence-imparting pigments. Hence, to produce enough opalescence in the composite, this translucent filler must be present in relatively high loadings. More particularly, the composite of the present invention should comprise about 20–86% by weight of a translucent filler, with 15–80% by volume, and preferably 25–80% by volume, of this filler component being in the 0.2–0.6 μm particle size range. The particle size of the individual particles may be measured by any known method, such as laser scattering described below. The composite of the present invention may be of the hybrid type, further containing a microfill having a mean particle size less than about 0.05 μm in a curable resin, preferably a photopolymerizable resin containing methacrylate monomers. Such methacrylate monomer resins are cured when exposed to visible light. The dental composite is applied to teeth by the dental practitioner and exposed to a visible light source to cure the resin. The cured composite of the present invention displays opalescence similar to that of natural tooth.

In a composite material, such as a tooth colored dental restorative, the resin matrix and the filler should be matched in their refractive index to achieve a transparency similar to tooth structure, as opposed to clear or opaque materials. In addition, this transparency is necessary for the material to be cured using visible light initiation of polymerization. The formulator has relatively wide choices for adjusting the refractive index of the resin because resins in the range of about 1.45 to about 1.60 are easily available commercially. Although glass fillers are much more complex to formulate, micron-sized particulate fillers may be manufactured to have a refractive index in the 1.45–1.60 range. Moreover, the purity of the glass filler should be very high because small amounts of impurities, down to the low ppm level, show very prominently when the filler is dispersed in the resin. Thus, in accordance with the principles of the present invention, the refractive index of the polymerized resin is the same or similar to the refractive index of the filler. More specifically, it is preferred that the refractive indices be within +/–0.04.

Translucent fillers suitable for use in the present invention include, but are not limited to, borosilicate glass, barium magnesium aluminosilicate glass, barium aluminosilicate glass, amorphous silica, zirconium silicate, titanium silicate, barium oxide, quartz, alumina and other inorganic oxide particles.

In one embodiment of the present invention, the translucent filler of the present invention has a mean particle size of about 0.1 μm to about 1.0 μm, with 15–80% by volume of this filler falling within the particle size range of 0.2–0.6 μm. In another embodiment of the present invention, the translucent filler is that described in copending application Ser. No. 09/270,999, but with 15–80% by volume of the filler falling within the 0.2–0.6 μm particle size range. Such a composite having a filler with a mean particle size of 0.05–0.5 μm with 15–80% by volume of that filler in the 0.2–0.6 μm particle size range will provide the high strength required for load bearing restorations, will maintain a glossy appearance in clinical use, and will have a vital, opalescent, translucent appearance.

To provide translucent filler having sufficient particles in the particle size range of 0.2–0.6 μm, a chemical sol gel process may be used to manufacture the filler, or preferably, a filler may be ground to the size range by an extensive comminution step. Comminution is preferably performed by wet milling either in an agitator mill or in a vibratory mill. Comminution deagglomerates the filler particles by separating particles from clusters, decreases the size of the filler particles, eliminates large particles by breakage and increases the specific surface area of the filler particles by producing a large quantity of fine particles.

The degree of opalescence may be measured by a simple colorimetric method similar to that disclosed in European Publication No. 533,434. The method described therein uses the b* yellowness/blueness color coordinate of the 1976 Cie L*a*b* space, referred to as the CIELAB scale, as described in Billmeyer & Saltzman, *Principles of Color Technology*, $2^{nd}$ Ed., pp. 62–65 (1981). In this color space, L* represents lightness, a* represents redness or greenness, and b* represents yellowness or blueness. This method defines color differences in relation to a reference standard. Thus, $\Delta L^* = L^*_{batch} - L^*_{standard}$; $\Delta a^* = a^*_{batch} - a^*_{standard}$; and $\Delta b^* = b^*_{batch} - b^*_{standard}$. A positive Δ value refers to the color difference of the test specimen (batch) being lighter, less green or less blue, respectively, than the reference, and a negative Δ value refers to the color difference of the test specimen being darker, less red or less yellow, respectively, than the reference. In addition to redness/greenness (a*), yellowness/blueness (b*) and lightness (L*), colors can also be described by their by hue (H*) or chroma (C*). For judging the direction of the color difference between two colors, it is useful to omit the L* dimension and use the chromaticity difference, ΔC*. *The Color Sphere™ Color System User's Guide*, pp. 4–1 to 4–23 (BYK Gardner 1994), which is the User's Guide for the TCS Plus apparatus used in Example 1 discussed below, discusses the method of measuring chromaticity differences, ΔC*, between a batch sample and a reference standard as a function of $\Delta a^*$ ($a^*_{batch} - a^*_{reference}$) and $\Delta b^*$ ($b^*_{batch} - b^*_{reference}$). Thus, $\Delta C^* = [(\Delta a^*)^2 + (\Delta b^*)^2]^{1/2}$.

In European Publication No. 533,434, aΔb* value was introduced as the value of the b* color coordinate of a 1 mm thick sample in the transmission mode minus that of the reflection mode. Thus, $\Delta b^*_{T-R} = b^*_{Transmission} - b^*_{Reflection}$. The b* color coordinates for standard daylight conditions were measured using a "DIANO MATCH SCAN II color computer (Bausch & Lomb Inc.) with a 2.5 mm diameter sample port. The b* transmission color coordinates were obtained using a standard white color tile in the reflection sample port, and the b* reflection color coordinates were obtained using the standard black color tile behind the sample. The 1976 Cie b* scale was selected to measure opalescence because it can quantitatively measure the difference between the blue observed by reflected light and orange observed in transmitted light. Since blue and yellow by definition are on opposite ends of the b* scale, Δb* will be a larger finite number if the sample is opalescent. Conversely, if the sample is not opalescent, it will reflect and transmit the same color, and Δb* would be zero or a smaller number. In the European publication, a Δb* value for the composite containing the opalescence-imparting additive of greater than 9 above a composite containing no opalescence-imparting additive is described as opalescent.

Δb* by this definition is of the same mathematical form but not the same parameter as the Δb* defined by the User'Guide for the TCS Plus. The User's Guide discusses measuring color differences between a test specimen and a reference standard, whereas the European publication attempts to measure a color difference or opalescence on the same 1 mm thick sample in the transmission mode minus the reflection mode, and then compares that difference to a standard. Both publications use the 1976 CIELAB color coordinates to measure the color differences. Knowing the scale to be used, apparatuses such as the TCS Plus used in Example 1 below and the DIANOMATCH SCAN II used in EP No. 533,434 calculated the color space coordinates based upon mathematical derivations and formulas upon which the CIELAB scale is based, which derivations are well known and available to one of ordinary skill in the art. For example, Billmeyer & Saltzman, *Principles of Color Technology*, 2nd Ed., pp 62–65 (1981), as cited in EP 533,434 provides equations for L*, a*, b* and $C^*_{ab}$, as does the TCS Plus User's Guide.

Opalescence in transmitted light is described as an orange effect, which also contains a red component that is best measured by the CIELAB coordinate a*. Thus, for the method used in the present invention for determining opalescence, the chromaticity difference, $\Delta C^*_{T-R}$, is used. $\Delta C^*_{T-R}$ includes, in addition to $\Delta b^*_{T-R}$ the red-green chromaticity difference, $\Delta a^*_{T-R}$. In this case, $\Delta a^*_{T-R}$ is the red-green equivalent of $\Delta b^*_{T-R}$. $\Delta C^*_{T-R}$ is a scalar quantity, and it is determined by taking the square root of the sum of $\Delta a^{*2}_{T-R}$ and $\Delta b^{*2}_{T-R}$. To differentiate from other color difference designations, the subscripts T for transmission and R for reflection are introduced. Thus, $\Delta a^*_{T-R}$=a* (Transmission mode)−a*(Reflection mode); $\Delta b^*_{T-R}$=b* (Transmission mode )−b*(Reflection mode); and $\Delta C^*_{T-R}$= $[(\Delta a^*_{T-R})^2+(\Delta b^*_{T-R})^2]^{1/2}$. It is noted that $\Delta C^*_{T-R}$ by this definition is not quite the same as the ΔC* defined by differences between a reference standard and test specimen, but rather is an extension of the method used in EP No. 533,434 involving differences between transmission and reflectance modes in a single test specimen, but further includes the chroma contributions from a* in addition to b*. At $\Delta C^*_{T-R}$ values less than 4, opalescence is not observed. For dental restorative composites to match the vitality of a natural tooth, the $\Delta C^*_{T-R}$ coordinate is advantageously at least about 9. At $\Delta C^*_{T-R}$ values between 4 and 9, some opalescence may be observed, but it is only slightly discernable by the naked eye. This low degree of opalescence in the restoration does not result in a vital looking appearance similar to natural tooth. At $\Delta C^*_{T-R}$ values of at least about 9, this opal effect is clearly observable by the naked eye, just as this effect is observable in connection with natural tooth. The higher the $\Delta C^*_{T-R}$ value the more pronounced the opal effect becomes.

EXAMPLES

In preparing the filler for incorporation into a composite paste, the mean particle size of the filler was measured by laser scattering. Laser scattering is a method of measuring mean particle size by sensing the average relative angular intensity of scattered light. A beam of monochromatic light with a uniform wave front is directed at the sample, the light is diffracted or scattered by the particles and a detector is used to measure the relative average intensity of the scattered light at various angles. The mean particle size and particle size distribution curve may then be calculated from the relative average intensity. One such laser scattering device is disclosed in U.S. Pat. No. 5,610,712 to Schmitz et al., incorporated herein by reference in its entirety. For the present examples, a Horiba Model LA-910 Laser Scattering Mean Particle Size Analyzer was used. The particle size distribution and mean particle size for each of the fillers was measured and the cumulative volume percent of filler particles distributed in the 0.2–0.6 μm particle size range was calculated from the particle size distribution curves.

The fillers used in the composites of the present invention are preferably silanated. For the following examples, the fillers were silanated by spraying in a V-blender with a 20% hydrolyzed solution of gamma-methacryloxypropyltrimethoxysilane in water to make the filler powder hydrophobic. The loading of the silane in the filler was 2.5% by weight.

The properly sized translucent filler may be combined with colloid sized particles, such as types of silica, alumina and silicates, for example silica zirconia or silica titania, the particles having a mean particle size less than 0.05 μm to form a hybrid composite, if desired. Typically, hydrophobic filmed silica is used in an amount between 1–15 wt % of the final composition.

The translucent filler, and optional colloidal filler is then combined with a light-curable resin base material which may include commercially available monomers containing methacrylate groups. TABLES 1 and 2 list the components of the resins that will be used in later examples.

TABLE 1

RESIN COMPOSITION A

| COMPONENT | % BY WEIGHT |
| --- | --- |
| BisGMA (Bisphenol A Diglycidyl ether dimethacrylate) | 3.0 |
| Triethylene Glycol Dimethacrylate | 24.7 |
| Ethoxylated Bisphenol A Dimethacrylate | 71.1 |
| 2-Ethylhexyl-4-(dimethylamino)benzoate | 0.49 |
| Camphoroquinone | 0.17 |
| 2-Hydroxy-4-methoxy Benzophenone | 0.49 |
| (BHT) Butylated Hydroxytoluene | 0.05 |

TABLE 2

RESIN COMPOSITION B

| COMPONENT | % BY WEIGHT |
| --- | --- |
| UDMA (7,7,9-Trimethyl-4,13-dioxo-3,14-dioxa-5,12-diazahexadecane-1,16,-dimethacrylate) | 42.7 |
| Hexanediol Dimethacrylate | 43.9 |
| Ethoxylated Bisphenol A Dimethacrylate | 13.0 |
| 2-Ethylhexyl-4(dimethylamino)benzoate | 0.25 |
| Camphoroquinone | 0.15 |

Other monomers may be used in the resin composition, such as diethylene glycol dimethacrylate, triethylene glycol dimethacrylate, tetraethylene glycol dimethacrylate, 1,6-hexanediol dimethacrylate, 1,12-dodecanediol dimethacrylate, diurethane dimethacrylate (Rohamere 6661-0, Huls America, Somerset, N.J.), trimethylolpropane trimethacrylate, glyceryl dimethacrylate, and neopentylglycol dimethacrylate.

The resin composition is introduced into a planetary mixer thermostated at 50° C. The planetary mixer is then started and the filler (or fillers) is added slowly over a period of 3 hours. The composite is subsequently mixed for another hour and then de-aerated under attenuated oxygen pressure.

Samples having the dimensions of 1 mm thick×2 inches diameter were then prepared in stainless steel molds sandwiched between glass slides. The samples were light cured for 10 minutes in a Cure Plus curing light (Jeneric Pentron Inc.) and additionally heat cured for 10 minutes at 135° C. in a Belleglass Curing Unit (Kerr Corp.). The chromaticity coordinates for standard daylight conditions were measured for each cured disk in the transmission and reflectance modes using a TCS Plus Colorimeter (BYK Gardner Inc.).

Example 1

Control Samples 1 and 2, and Test Samples 1–3 were prepared as described above, using silane treated borosilicate glass as the translucent filler, differing only in mean particle size and distribution. Control Sample 2 also contains 0.1% by weight titanium dioxide (type P25 from Degussa Corp., Ridgefield Park, N.J.), a known opalescence-imparting pigment. Borosilicate glass has a refractive index of about 1.48. Each translucent filler was mixed with Resin Composition B, as provided in Table 2, with the translucent filler loading being 74% by weight of the total composition. Resin Composition B has a refractive index of 1.478, and thus the refractive indices of the filler and resin are within 0.002 of each other. TABLE 3 provides the cumulative volume percent of the translucent filler falling within the 0.2–0.6μm particle size range and the resulting $\Delta C^*_{T-R}$ value.

TABLE 3

OPALESCENCE OF BOROSILICATE GLASS

| Sample # | Mean Particle Size (μm) | Cumulative Vol. % Filler in 0.2– 0.6 μm Range | $\Delta C^*_{T-R}$ (standard deviation) |
|---|---|---|---|
| Control # 1 | 10.0 | 1.3 | 5.19 (0.05) |
| Control # 2 w/ opalescent additive | 1.0 | 40.4 | 21.12 (0.22) |
| Test # 1 | 1.0 | 40.4 | 15.89 (0.10) |
| Test # 2 | 0.55 | — | 14.10 (0.39) |
| Test # 3 | 0.4 | 78.3 | 15.32 (0.21) |

As TABLE 3 demonstrates, where the mean particle size is large and the distribution is such that a low percentage falls within the 0.2–0.6 μm particle size range, as in Control Sample 1, the composite displays low opalescence, less than that required to simulate natural tooth and less than that required for the "opal effect" to be visible to the naked eye. The low opalescence is believed to be due to weak diffuse interaction with light, such that there is a small amount of light scattering. In contrast, Test Samples 1–3 are clearly opalescent, having $\Delta C^*_{T-R}$ values well above 9. Although the opalescence is not as dramatic as in Control Sample 2, which contains the opalescence-imparting pigment, it is clearly discernible to the naked eye and the restorations made from these test composites display vitality similar to natural tooth.

Example 2

Control Sample 3 and Test Samples 4 and 5 were prepared as described above, using silane treated barium aluminosilicate glass as the translucent filler, differing only in mean particle size and distribution. Barium aluminosilicate glass has a high refractive index of about 1.54, and contains a heavy metal, barium, to impart x-ray radiopacity to the restoration. Each translucent filler was mixed with Resin Composition A, as provided in Table 1, with the translucent filler loading being 78% by weight of the total composition. Resin Composition A has a refractive index of 1.518, and thus the refractive indices of the filler and resin are within 0.022 of each other. TABLE 4 provides the cumulative volume percent of the translucent filler falling within the 0.2–0.6 μm particle size range and the resulting $\Delta C^*_{T-R}$ value.

TABLE 4

OPALESCENCE OF BARIUM ALUMINOSILICATE GLASS

| Sample # | Mean Particle Size (μm) | Cumulative Vol. % Filler in 0.2– 0.6 μm Range | $\Delta C^*_{T-R}$ (standard deviation) |
|---|---|---|---|
| Control # 3 | 10.0 | 4.0 | 7.98 (0.44) |
| Test # 4 | 1.0 | 31.4 | 15.80 (0.11) |
| Test # 5 | 0.4 | 67.7 | 15.58 (0.42) |

As TABLE 4 demonstrates, Control Sample 3 having a slightly higher loading of barium aluminosilicate translucent filler distributed in the 0.2–0.6 μm particle size range than the borosilicate glass of Control Sample 1 has some degree of opalescence, which is slightly discernible by the naked eye, but as the mean particle size is reduced and a larger amount of particles fall within the 0.2–0.6 μm particle size range, the degree of opalescence increases significantly and is more clearly visible by the naked eye.

Example 3

Test Samples 6–9 were prepared as described above, using different translucent fillers of varying mean particle size and filler loadings. Silica (OX-50 from Degussa Corp.), used in Test Samples 6 and 7, has a refractive index of about 1.45. The translucent silica filler was mixed with Resin Composition B, as provided in Table 2, with the translucent filler loading as listed in TABLE 5. Resin Composition B has a refractive index of 1.478, and thus the refractive indices of the silica filler and resin are within 0.028 of each other. The titanium silicate filler of Test Sample 8 (from Tokuyama, Japan) was mixed with Resin Composition B, while the zirconium silicate filler of Test Sample 9 (from Tokuyama, Japan) was mixed with Resin Composition A. These silicate fillers comprise nanoparticles produced by the sol gel process, and the refractive index was not measured. TABLE 5 provides the total filler loading for the composite formulation, the cumulative volume percent of the translucent filler falling within the 0.2–0.6 μm particle size range and the resulting $\Delta C^*_{T-R}$ value.

TABLE 5

OPALESCENCE OF OTHER GLASSES

| Sample # | Mean Particle Size (μm) | Filler Loading (Wt. %) | Cumulative Vol. % Filler in 0.2– 0.6 μm Range | $\Delta C^*_{T-R}$ (standard deviation) |
|---|---|---|---|---|
| Test # 6 | 0.04 | 20 | 15.9 | 9.52 (0.73) |
| Test # 7 | 0.4 | 40 | 60.8 | 24.58 (0.94) |
| Test # 8 | 0.2 | 74 | 54.5 | 18.96 (0.37) |
| Test # 9 | 0.2 | 74 | 64.4 | 11.71 (0.40) |

As TABLE 5 demonstrates, silica fillers produce opalescence that is discernible in varying degrees to the naked eye, with the degree of opalescence being dependent upon the mean particle size and loading. The 0.04 μm silica filler produced a $\Delta C^*_{T-R}$ value of 9.52 with a filler loading of only 20% by weight in which 15.9% by volume of this filler has particles in the 0.2–0.6 μm particle size range. While this degree of opalescence is visible to the naked eye, the 0.4 μm agglomerated silica filler having a higher loading of 40% by weight in which a high amount of the filler falls within the 0.2–0.6 μm particle size range produced a much stronger degree of opalescence as indicated by the $\Delta C^*_{T-R}$ value of 24.58. The titanium silicate and zirconium silicate formulas having still higher loadings, 74% by weight, with a high amount of the filler falling withing the 0.2–0.6 μm range also displayed relatively high degrees of opalescence.

From the examples described above, it appears that high distributions of translucent filler particles either below 0.2 μm or above 0.6 μm result in low opalescence. This is believed to be due to these particles not having a sufficiently strong interaction with light to produce light scattering, which produces the "opal effect." Particles within the 0.2–0.6 μm particle size range have a strong diffuse interaction with light. If present in sufficient amounts in the composite, these particles will produce a high degree of opalescence that is clearly visible to the naked eye, giving a dental restoration made from this composite a vital-looking appearance.

Example 4

Test Samples 10–13 were prepared as described above, using silane treated 0.4 μm barium aluminosilicate glass, differing only in tint, or color shade. Test Sample 5 from Table 4 is an untinted composite paste, meaning that it contains no color pigments to shade the composite. Test Samples 10–13 contain yellow hue pigments to match the color of the cured composite to the color of natural teeth. Two different commercially available yellow hue pigments were used, namely FDC#6 from Warner Jenkinson, Inc. and YO1987 from Pfizer Inc. The filler used in the composite paste of Test Sample 10 contains 50% by weight untinted filler and 50% by weight of filler tinted with the yellow hue pigments to create a Vita Shade A3 color, according to the known shading system used in the dental industry for matching the color of natural teeth. The fillers used in the composite pastes of Test Samples 11, 12 and 13 contain 75%, 90% and 100% by weight tinted filler, respectively. Each translucent filler was mixed with Resin Composition A, as provided in Table 1, with the translucent filler loading being 78% by weight of the total composition, and with the cumulative volume percent of the translucent filler falling within the 0.2–0.6 μm particle size range being 67%. TABLE 6 provides the weight percent of yellow pigment used in the composite paste and the resulting $\Delta C^*_{T-R}$ value.

TABLE 6

OPALESCENCE OF TINTED BARIUM ALUMINOSILICATE GLASS

| Sample # | Filler | FDC#6 (Wt. %) | YO1987 (Wt. %) | Total Pigment in Paste (Wt. %) | $\Delta C^*_{T-R}$ (standard deviation) |
|---|---|---|---|---|---|
| Test # 5 | 100% 0.4 μm untinted | 0 | 0 | 0 | 12.45 (0.08) |
| Test # 10 | 50% 0.4 μm untinted 50% 0.4 μm tinted | 0.0002 | 0.001 | 0.0012 | 11.37 (0.15) |
| Test # 11 | 25% 0.4 μm untinted 75% 0.4 μm tinted | 0.0003 | 0.0015 | 0.0018 | 10.17 (0.33) |
| Test # 12 | 10% 0.4 μm untinted 90% 0.4 μm tinted | 0.00036 | 0.0018 | 0.00216 | 8.82 (0.16) |
| Test # 13 | 100% 0.4 μm tinted | 0.0004 | 0.002 | 0.0024 | 7.43 (0.15) |

TABLE 6 demonstrates the effect of color pigments on opalescence. Opalescence observed in teeth and restorative materials is a subtle effect that may be affected by other more dominant optical properties. For example, opalescence may be significantly affected, or masked, by color or shade. In particular, hues in the range of yellow and blue from pigmentation are believed to affect opalescence significantly if sufficient chroma is present. Composite resin formulas shaded to match the yellow hue present in natural teeth, for example the Vita Shade A3 formula, may mask opalescence because of the strong yellow chroma in the b* coordinate. Test Samples 5 and 10–13 have identical components with the exception of the addition of varying quantities of a yellow hue pigmentation in Test Samples 10–13. As TABLE 6 demonstrates, opalescence decreases with increasing shading of the composite paste. The untinted composite had a $\Delta C^*_{T-R}$ value of 12.45 and the opalescence was clearly discernible. Test Samples 10 and 11 contained small quantities of pigment, less than about 0.0021% by weight of the total composition, and had $\Delta C^*_{T-R}$ values of 11.37 and 10.17, respectively, which again the opalescence is clearly discernible by the naked eye, but not to as high a degree as the untinted composite. Test Sample 12 contained a higher amount of pigment, 0.00216% by weight of the total composition, and had a $\Delta C^*_{T-R}$ value of 8.82, which opalescence is only borderline visible by the naked eye. Test Sample 13 had a relatively high amount of pigment resulting in a $\Delta C^*_{T-R}$ value of only 7.43, which is less than that needed for the opalescence to be clearly visible to the naked eye. Without being bound by theory, as pigments are added to the composite formula to produce a Vita A3 shade, the yellow-brown hue becomes dominant and opalescence is not discernible anymore. This may explain why opalescence has not been previously observed in dental restorative composites without the addition of opalescence-imparting agents. To maximize the opalescent effect from reinforcing translucent fillers, it is believed that the restorative composite formulations should be relatively colorless, much like human enamel. To this end, the amount of yellow hue pigmentation added to the composite formulations should advantageously be kept at a level at or below about 0.0021% by weight. To express this in an alternative way, the composition should be less than 90% A3 shaded.

Example 5

In addition to providing opalescence, the composites of the present invention are also translucent. A translucency, as measured by % T, that matches the natural tooth structure ranges from 14–80% T. The % T is measured from a 1 mm thick cured sample by a Gardner XL10 Color Difference Meter (BYK Gardner Inc.). TABLE 7 provides the % T values for the untinted test samples of the present invention.

TABLE 7

TRANSLUCENCY OF RESTORATIVE COMPOSITIONS

| Test Sample #'s | Paste Components | Refractive Index of Filler | Refractive Index of Resin | Filler Loading (Wt. %) | % T |
|---|---|---|---|---|---|
| 1, 2, 3 | Borosilicate glass in Resin B | 1.48 | 1.478 | 74.0 | 25–35 |
| 4, 5 | Barium alumino-silicate in Resin A | 1.54 | 1.518 | 78.0 | 26–33 |
| 6, 7 | Silica in Resin B | 1.45–1.48 | 1.478 | 20–40 | 73–84 |
| 8 | Titanium silicate in Resin B | * | 1.478 | 74.0 | 73 |
| 9 | Zirconium silicate in Resin A | * | 1.518 | 74.0 | 23 |

*Refractive index not measurable.

As TABLE 7 shows, the Test Samples of the present invention have a translucency that is the same or substantially similar to that of natural tooth.

Thus, the dental composite of the present invention provides a translucent restoration having a high degree of opalescence that is clearly discernible by the naked eye. Opalescing agents need not be added to provide the vital looking appearance of natural tooth, as the restorative composite of the present invention is self-opalescing.

While the present invention has been illustrated by a description of various embodiments and while these embodiments have been described in considerable detail, it is not the intention of the Applicants to restrict or in any way limit the scope of the appended claims to such detail. Additional advantages and modifications will readily appear to those skilled in the art. The invention in its broader aspects is therefore not limited to the specific details and representative composition as shown and described. This has been a description of the present invention, along with the preferred composition using the present invention as currently known. However, the invention itself should only be defined by the appended claims.

What is claimed is:

1. A dental restorative composite, comprising:
   a resin base; and
   an inorganic filler consisting essentially of:
   (a) a translucent filler in an amount of about 20% to about 86% by weight of the composite, the translucent filler consisting of particles of a mean particle size between about 0.05 μm and 0.5 μm and comprising between about 15% and about 80% by volume of particles in a particle size range from about 0.2 μm to about 0.6 μm, and
   (b) a colloidal filler in an amount up to about 15% by weight of the composite, the colloidal filler consisting of particles of a mean particle size less than about 0.05 μm;
   wherein the translucent filler contributes to the dental restorative composite an average $\Delta C^*_{T-R}$ coordinate of at least about 9.

2. The dental restorative composite of claim 1, wherein the dental restorative composite is substantially free of components, other than the inorganic filler, that have the effect of imparting opalescence to the composite.

3. The dental restorative composite of claim 1, wherein the translucent filler comprises between about 25% and about 80% by volume of particles in a particle size range from about 0.2 μm to about 0.6 μm.

4. The dental restorative composite of claim 1, wherein the translucent filler and the resin base each have a refractive index in the range of about 1.45–1.60.

5. The dental restorative composite of claim 1, wherein the translucent filler has a refractive index within +/−0.04 of the refractive index of the resin base.

6. The dental restorative composite of claim 1, wherein the composite includes less than about 0.0021% by weight yellow hue pigments.

7. The dental restorative composite of claim 1, wherein the translucent filler is selected from the group consisting of: borosilicate glass, barium aluminosilicate glass, silica, titanium silicate, zirconium silicate, barium magnesium aluminosilicate glass, barium oxide, quartz and alumina.

8. The dental restorative composite of claim 1, wherein the restorative composite comprises about 1–15% by weight of the colloidal filler.

9. The dental restorative composite of claim 1, wherein the translucent filler has a mean particle size of about 0.4 μm.

10. The dental restorative composite of claim 9, wherein the restorative composite comprises about 1%–15% by weight of the colloidal filler.

11. A dental restorative composite, comprising:
    a resin base; and
    a translucent filler comprising between about 15% and about 80% by volume of particles in a particle size range from about 0.2 μm to about 0.6 μm,
    wherein the translucent filler has a mean particle size from about 0.05 μm to about 0.5 μm, and
    wherein the translucent filler contributes to the dental restorative composite an average $\Delta C^*_{T-R}$ coordinate of at least about 9.

12. The dental restorative composite of claim 11, further comprising about 1%–15% by weight of a microfiller of mean particle size less than about 0.05 μm.

13. A dental restorative composite comprising:
    a resin base having a refractive index in the range of about 1.45–1.60; and
    an inorganic filler consisting essentially of:
    (a) a translucent filler having a refractive index in the range of about 1.45–1.60 in an amount of about 20% to about 86% by weight of the composite, the translucent filler having a mean particle size between about 0.05 μm and 0.5 μm and comprising between about 15% and about 80% by volume particles in a particle size range from about 0.2 μm to about 0.6 μm, and
    (b) a colloidal filler in an amount up to about 15% by weight of the composite, the colloidal filler having a mean particle size less than about 0.05 μm;
    wherein the translucent filler contributes to the dental restorative composite an average $\Delta C^*_{T-R}$ coordinate of at least about 9, and
    wherein the refractive index of the translucent filler is within +/−0.04 of the refractive index of the resin base.

14. The dental restorative composite of claim 13, wherein the dental restorative composite is substantially free of components, other than the inorganic filler, that have the effect of imparting opalescence to the composite.

15. The dental restorative composite of claim 13, wherein the translucent filler comprises between about 25% and about 80% by volume of particles in a particle size range from about 0.2 µm to about 0.6 µm.

16. The dental restorative composite of claim 13, wherein the composite includes less than about 0.0021% by weight yellow hue pigments.

17. The dental restorative composite of claim 13, wherein the translucent filler is selected from the group consisting of: borosilicate glass, barium aluminosilicate glass, silica, titanium silicate, zirconium silicate, barium magnesium aluminosilicate glass, barium oxide, quartz and alumina.

18. The dental restorative composite of claim 13, wherein the translucent filler has a mean particle size of about 0.4 µm.

19. The dental restorative composite of claim 13 wherein the restorative composite comprises about 1%–15% by weight of the colloidal filler.

20. A dental restorative composite comprising:
   a resin base having a refractive index in the range of about 1.45–1.60; and
   20% to 86% by weight translucent filler having a refractive index in the range of about 1.45–1.60, the translucent filler comprising between about 15% and about 80% by volume particles in a particle size range from about 0.2 µm to about 0.6 µm,
   wherein the translucent filler has a mean particle size from about 0.05 µm to about 0.5 µm, and
   wherein the translucent filler contributes to the dental restorative composite an average $\Delta C^*_{T-R}$ coordinate of at least about 9, and
   wherein the refractive index of the translucent filler is within +/−0.04 of the refractive index of the resin base.

21. The dental restorative composite of claim 20, further comprising about 1%–15% by weight of a microfiller of mean particle size less than about 0.05 µm.

22. The dental restorative composite of claim 11, wherein the dental restorative composite is substantially free of components, other than the translucent filler, that have the effect of imparting opalescence to the composite.

23. The dental restorative composite of claim 11, wherein the translucent filler comprises between about 25% and about 80% by volume of particles in a particle size range from about 0.2 µm to about 0.6 µm.

24. The dental restorative composite of claim 11, wherein the translucent filler and the resin base each have a refractive index in the range of about 1.45–1.60.

25. The dental restorative composite of claim 11, wherein the translucent filler has a refractive index within +/−0.04 of the refractive index of the resin base.

26. The dental restorative composite of claim 11, wherein the composite includes less than about 0.0021% by weight yellow hue pigments.

27. The dental restorative composite of claim 11, wherein the translucent filler is selected from the group consisting of: borosilicate glass, barium aluminosilicate glass, silica, titanium silicate, zirconium silicate, barium magnesium aluminosilicate glass, barium oxide, quartz and alumina.

28. The dental restorative composite of claim 11, wherein the restorative composite comprises between about 20% and about 86% by weight translucent filler.

* * * * *

UNITED STATES PATENT AND TRADEMARK OFFICE
CERTIFICATE OF CORRECTION

PATENT NO.    : 6,232,367 B1
DATED         : May 15, 2001
INVENTOR(S)   : Kobashigawa et al.

It is certified that error appears in the above-identified patent and that said Letters Patent is hereby corrected as shown below:

Column 6,
Line 39, reads "by their by hue" and should read -- by their hue --.
Line 50, reads "a$\Delta$b" and should read -- a $\Delta$b --.
Line 56, reads "a 2.5 mm" and should read -- a 25 mm --.

Column 7,
Line 8, reads "User' Guide" and should read -- User's Guide --.
Line 18, reads "calculated the color" and should read -- calculate the color --.

Column 8,
Line 25, reads "filmed silics" and should read -- fumed silica --.

Column 11,
Line 60, reads "(standard deviation" and should read -- (standard deviation) --.

Column 12,
Line 8, reads "(standard deviation" and should read -- (standard deviation) --.

Column 11,
Table 6, the text of Test #11 should remain together in one column or the other.

Signed and Sealed this

Nineteenth Day of March, 2002

Attest:

JAMES E. ROGAN
*Director of the United States Patent and Trademark Office*

*Attesting Officer*